United States Patent [19]

Carobbi et al.

[11] Patent Number: 4,978,397
[45] Date of Patent: Dec. 18, 1990

[54] PROCESS FOR PREPARING HIGH-PURITY LACTULOSE SYRUP AND THE SYRUP OBTAINED

[76] Inventors: Renato Carobbi, via Dalmazia 168, Pistoia; Franco Innocenti, via Repubblica Val d'Ossola 3, Bagno a Ripoli (FI), both of Italy

[73] Assignee: SIRAC Srl. Milano, ITALY

[21] Appl. No.: 344,444

[22] Filed: Apr. 27, 1989

Related U.S. Application Data

[63] Continuation of Ser. No. 149,158, Jan. 27, 1988, abandoned.

[30] Foreign Application Priority Data

Dec. 30, 1987 [IT] Italy ................................ 23265 A/87

[51] Int. Cl.$^5$ .......................... C13D 3/14; C13D 3/12
[52] U.S. Cl. .................................. 127/46.2; 127/46.3; 127/46.1; 127/55
[58] Field of Search .................... 127/46.1, 46.2, 46.3, 127/55

[56] References Cited

U.S. PATENT DOCUMENTS 4,565,582  1/1986  Filippini et al. .................. 127/46.1

FOREIGN PATENT DOCUMENTS 865594  4/1961  United Kingdom .

OTHER PUBLICATIONS

Yurkevich et al., "Study of the Interaction of Polyols with Polymers Containing N–Substituted [(4–Botonophenyl)methyl]ammonio Groups," 43 Carbohydrate Research 215–224, (1975).

*Primary Examiner*—Chung K. Pak
*Attorney, Agent or Firm*—Parkhurst, Wendel & Rossi

[57] ABSTRACT

A process for preparing high-purity lactulose by the following stages:
(a) diluting with water to a concentration of 15–25% a syrup containing 45–55% of lactulose and having a lactulose content on a dry substance basis of between 74 and 82% w/w;
(b) pretreating the diluted syrup with bromine or bifunctional boron resins;
(c) treating the pretreated syrup from stage (b) with ion exchange resins of strong anion type under conditions such that the pH of the percolated syrup is between 8 and 10.

3 Claims, No Drawings

PROCESS FOR PREPARING HIGH-PURITY LACTULOSE SYRUP AND THE SYRUP OBTAINED

This is a continuation of application Ser. No. 07/149,158, filed Jan. 27, 1988, now abandoned.

FIELD OF THE INVENTION

This invention relates to a process for preparing high-purity lactulose syrup by purifying lactulose syrup containing extraneous carbohydrates such as lactose, galactose and the like, and to the syrup obtained.

PRIOR ART

Lactulose is a synthetic disaccharide used in syrup or crystalline form in the treatment of intestinal afflictions and hepatic disorders.

Commercially available lactulose syrup is generally impure and contains more or less large quantities of extraneous carbohydrates, particularly lactose and galactose, but also fructose, tagatose, epilactose and others not always easily identifiable.

A typical composition of currently available syrup is the following:

| | |
|---|---|
| lactulose | 50% by weight |
| galactose | 4–8% by weight |
| lactose | 4–8% by weight |
| other carbohydrates | 5–10% by weight |

Lactulose syrup also generally contains other impurities in the form of sugar conversion products such as lactones and aldonic acids.

The extraneous carbohydrates or the other impurities are undesirable in the therapeutic applications for which the lactulose is intended.

There is therefore a requirement for lactulose in syrup or crystalline form of much higher purity in which the extraneous carbohydrate content has been reduced as much as possible.

The main lactulose purification processes known up to the present time are based either on selective absorption on ion exchange resins of known type or on controlled oxidation of the syrup with bromine to convert the galactose and lactose into the corresponding aldonic acids which are then eliminated by treatment with normal ion exchange resins.

A purification process of the first type is described for example in French patent no. 2,117,558 in which the separation is implemented by feeding the lactulose syrup over an ion exchange resin of bisulphite or sulphite type.

Processes of this type have not found industrial application mainly because of their duration and cost. Again, in no case do they result in high purification.

The second type of purification is described in USA patent No. 3,272,705 and British patent No. 865,594 in which the lactulose syrup is treated with bromine chemically or electrochemically to produce aldose oxidation. The oxidised syrup is then passed through resins. The syrups obtained by this process are always too impure.

It is also known to use boron resins for carbohydrate separation, but only in chromatographic analytical methods. The boron resins used in these processes are very unstable both chemically and mechanically.

Much more efficient processes have been described by the present applicant in Italian patent applications No. 21689 A/83 and 20176 A/84, which are based on treating commercial lactulose syrups with bromine and with new bifunctional boron resins respectively.

Using these processes, lactulose syrups are obtained having a purity on a dry substance basis of between 88 and 92% from commercial syrups having a dry substance purity of between 74 and 82%.

However a further improvement with the object of obtaining higher-purity syrups is desirable.

SUMMARY OF THE INVENTION

We have now discovered a process which, starting from syrup containing 45–55% w/w of lactulose and having a lactulose content on a dry substance basis of 74–82% w/w, enables a syrup to be obtained with a lactulose content on a dry substance basis which exceeds 95% w/w.

The process according to the invention is characterised by diluting said syrup with water to a lactuose content of 15–25%, pretreating the resultant diluted syrup with bromine or bifunctional boron resins, and treating said pretreated syrup with ion exchange resins of strong anion type under such conditions that the pH of the percolated syrup is between 8 and 10.

These and other characteristics of the process according to the present invention will be more apparent from the detailed description given hereinafter for non-limiting illustration.

DETAILED DESCRIPTION OF THE INVENTION

Lactulose syrup containing 45–55% w/w of lactulose and having a lactulose content on a dry substance basis of between 74 and 82% w/w is firstly diluted with water to obtain a syrup with a lactulose content of 15–25% w/w.

This solution is pretreated with bromine or alternatively with bifunctional boron resins as described hereinafter.

The pretreatment with bromine is effected by adding bromine and an NaOH solution so as to maintain the pH between 7 and 8. Bromine is added until a bromine excess persists, and at this point sodium bisulphite is added to eliminate the excess bromine, the solution then being deionized by passage through strongly acidic and weakly basic ion exchange resins.

The pretreatment with bifunctional boron resins is effected using resins of type $$\text{(P)} - R - \overset{+}{N} R^1 R^2 - R^3 \diagup \!\!\!\!\!\!\bigcirc\!\!\!\!\!\!\diagdown B \diagup\!\!\!\!\!\!\!\!\! ^{OH}_{OH} \quad X^- \qquad (1)$$

in which P is a polyacrylic or polystyrene polymer matrix, R and $R^2$ are $(CH_2)_n$ where n is between 0 and 5, R′ and $R^2$ are $C_1$–$C_5$ alkyls and X— is an anion chosen from the group consisting of hydroxyl and halogens. The lactulose syrup is circulated through a column containing said resins which selectively absorb the lactulose. Syrup circulation is maintained for 1–3 hours at a throughput of 1–3 volumes/h of resin. The resin is then washed with water, eluted with an HCl solution and the product neutralized with weakly basic resin.

The syrup obtained by these pretreaments is then passed through strong anionic macroporous gell-type ion exchange resins under such conditions that the percolated syrup is of pH 8-10. Any strong anion resin may be used.

This treatment can be effected using columns with mixed resins (strong anion in OH− form and strong cation in H+ form) in which the required pH is determined by the composition of the mixed bed.

Alternatively, the treatment can be effected with a series of columns containing alternately strong anion and strong cation resins respectively, so obtaining the same results but avoiding the difficulties of regenerating mixed resins. The operation is performed with a syrup throughput of 6-8 volumes of hour per volume of resin, which ensures a percolated resin pH of 8-10.

As a further alternative, strong anion resins salified with weak acids ($CO_3^{2-}$, $HCO_3-$, $CH_3COO^-$, $HCOO^-$) with pH stabilized at 8-10 to maintain the same pH in the percolated syrup.

In this embodiment, the operation is performed with a syrup throughput of 1-2 volumes per hour per volume of resin, and in addition two ion exchange columns are connected in series to eliminate any ion released during the main process.

The syrup obtained by said treatments is finally concentrated to a lactulose content of about 50%.

This syrup has a lactulose content on a dry substance basis exceeding 95%.

The following examples of the preparation of high-purity lactulose syrup are given for illustrative purposes.

EXAMPLE 1

1000 g of commercial lactulose syrup having the following composition:

| | |
|---|---|
| lactulose | 51% |
| lactose | 4% |
| galactose | 5% |
| dry residue | 70% |
| lactulose as % of dry substance | 73% | are diluted with water to a lactulose concentration of 20%.

The syrup obtained is treated with bromine until an excess persists, the PH being kept at 7.0-8.0 by adding 1 N NaOH.

Sodium sulphite is then added to the syrup to eliminate the excess bromine, the syrup then being deionized though strongly acid and weakly basic ion exchange resins.

In this manner a syrup containing 17% of lactulose is obtained, having the following composition:

| | | |
|---|---|---|
| lactulose | 17% | |
| lactose | 0.01% | |
| galactose | 0.01% | syrup P |
| dry residue | 19.5% | |
| lactulose as % of dry substance | 87% | |

This syrup is then percolated through a column of 400 ml of strong anion resin in OH− form (Amberlite IRH 400) followed by a column of 400 ml of strong cation resin in H+ form (Amberlite IR 120) with a liquid throughput of 8 volumes per hour per volume of resin for 60 minutes. The pH of the percolated liquid is checked and is always between 8 and 10.

The syrup is finally concentrated to obtain 870 g of a syrup having the following composition:

| | |
|---|---|
| lactulose | 51.2% |
| galactose | 0.4% |
| lactose | 0.3% |
| dry residue | 53.5% |
| lactulose as % of dry substance | 95.7% |

EXAMPLE 2

1000 g of commercial 51% lactulose of the same batch as that used in Example 1 are treated with bromine as in Example 1 to obtain a syrup analogous to syrup P.

The syrup is then percolated through a column of 400 ml of resin in $CO_3^{2-}$ form (Amberlite IRA 900) followed by a column of 50 ml strongly acid resin (Amberlite IR 120) and a column of 50 ml of weakly basic resin in OH− form (Amberlite IRA 94S), at a throughput of 400 ml/h. The pH of the percolated liquid is between 8 and 10.

The syrup obtained is concentrated to obtain 920 g of syrup having the following composition:

| | |
|---|---|
| lactulose | 50.9% |
| galactose | 0.4% |
| lactose | 0.3% |
| dry residue | 53.5% |
| lactulose as % of dry substance | 95.2% |

EXAMPLE 3

1000 g of commercial lactulose syrup having the following composition:

| | |
|---|---|
| lactulose | 50.3% |
| lactose | 3.0% |
| galactose | 4.6% |
| dry residue | 61.4% |
| lactulose as % of dry substance | 82.0% | are diluted with water to a lactulose concentration of 20%.

The solution obtained is circulated through a 5 l column containing bifunctional boron resin of formula (I) as defined in the text, maintaining the circulation for 2 hours at a throughput of 2 volumes/h per volume of resin.

The resin is then washed with water and eluted with a 2 N HCl solution.

The eluted solution is treated with a weakly basic resin until neutral.

A lactulose solution is obtained having the following composition:

| | |
|---|---|
| lactulose | 12.20% |
| lactose | not determined |
| galactose | 0.05% |

| | |
|---|---|
| dry residue | 13.5% |
| lactulose as % of dry substance | 92.0% |

The solution is then percolated through a column of 400 ml of resin in OH⁻ form (Amberlite IRA 900) followed by a column of resin in H+ form (Amberlite IR 252) maintaining a circulating liquid throughput of 8 volumes per hour per volume of resin for 60 minutes. The pH of the percolated liquid is between 8 and 10.

The syrup treated in this manner is concentrated to obtain 890 g of a syrup having the following composition:

| | |
|---|---|
| lactulose | 50.3% |
| galactose | 0.3% |
| lactose | 0.1% |
| dry residue | 51.7% |
| lactulose as % of dry substance | 97.3 |

We claim:

1. A process for preparing high-purity lactulose, comprising:
   (a) diluting with water to a lactulose content of 15-25% weight by weight a syrup containing 45-55% weight by weight of lactulose and having a lactulose content on a dry substance basis of 74-85% weight by weight;
   (b) pretreating the syrup thus diluted with bifunctional boron resins of formula

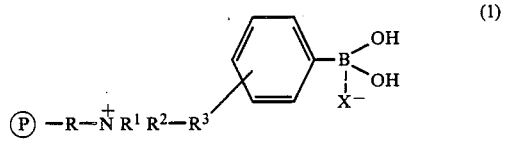

in which $\text{\textcircled{P}}$ is a polyacrylic or polystyrene polymer matrix, R and $R_3$ are $(CH_2)_n$ wherein n is between 0 and 5, $R'$ and $R_2$ are $C_1$-$C_5$ alkyls and $X-$ is an anion chosen from the group consisting of hydroxyl and halogens;
   (c) neutralizing the syrup from stage (b) with a weakly basic resin,
   (d) treating the syrup from stage (c) with ion exchange resins using a series of columns containing alternatively anion resins in OH form and cation resins in H+form respectively, the pH value of percolated syrup being maintained between 8 and 10 by controlling syrup throughput between 6 and 8 volumes per hour per volume of ion exchange resin or alternatively with a series of columns containing strong anion exchange resins salified with anions selected from the group consisting of $CO_3^{2-}$, $HCO_3^-$, $CH_3COO^-$ and $HCOO^{3-}$, wherein the pH of the percolated syrup is maintained between 8 and 10 by controlling the syrup throughput between 1 and 2 volumes per hour per volume of ion exchange resin.

2. A process as claimed in claim 8, characterized in that pretreating the diluted syrup with said boron resins is conducted by circulating said dilute syrup through a column containing said boron resins for 1-3 hours at a throughput of 1-3 volumes/h per volume of resin.

3. A process as claimed in claim 1, characterized in that the treatment with said ion exchange resins is conducted using columns with mixed anion resins in OH⁻ form and cation resins in H+ form, the pH of the percolated syrup being maintained between 8 and 10 by the composition of the mixed bed.

* * * * *

UNITED STATES PATENT AND TRADEMARK OFFICE
CERTIFICATE OF CORRECTION

PATENT NO. : 4,978,397

DATED : December 18, 1990

INVENTOR(S) : Renato CAROBBI et al.

It is certified that error appears in the above-identified patent and that said Letters Patent is hereby corrected as shown below:

ON TITLE PAGE:

[73] Assignee should read --INALCO Spa, Milano, ITALY-- rather than "SIRAC Srl, Milano, ITALY".

Signed and Sealed this

Twelfth Day of May, 1992

*Attest:*

DOUGLAS B. COMER

*Attesting Officer*  Acting Commissioner of Patents and Trademarks